(12) United States Patent
Wall

(10) Patent No.: US 12,419,676 B2
(45) Date of Patent: Sep. 23, 2025

(54) SURGICAL GUIDE AND METHODS OF USE

(71) Applicant: Warsaw Orthopedic, Inc., Warsaw, IN (US)

(72) Inventor: Daniel Paxton Wall, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 18/495,130

(22) Filed: Oct. 26, 2023

(65) Prior Publication Data

US 2024/0050141 A1 Feb. 15, 2024

Related U.S. Application Data

(62) Division of application No. 16/659,934, filed on Oct. 22, 2019, now Pat. No. 11,832,865.

(51) Int. Cl.
| | | |
|---|---|---|
| *A61B 17/90* | (2006.01) | |
| *A61B 17/02* | (2006.01) | |
| *A61B 17/17* | (2006.01) | |
| *A61B 34/10* | (2016.01) | |
| *A61B 34/20* | (2016.01) | |
| *A61B 34/30* | (2016.01) | |
| *A61B 50/20* | (2016.01) | |

(52) U.S. Cl.
CPC .......... *A61B 17/90* (2021.08); *A61B 17/0218* (2013.01); *A61B 17/17* (2013.01); *A61B 34/10* (2016.02); *A61B 34/20* (2016.02); *A61B 34/30* (2016.02); *A61B 50/20* (2016.02)

(58) Field of Classification Search
CPC ... A61B 17/90; A61B 17/17; A61B 2034/305; A61B 17/0218
See application file for complete search history.

(56) References Cited

U.S. PATENT DOCUMENTS

| | | | |
|---|---|---|---|
| 2010/0249526 A1* | 9/2010 | Shelton, IV | A61B 17/0293 600/208 |
| 2010/0298647 A1* | 11/2010 | Black | A61B 17/1703 600/210 |
| 2017/0143326 A1* | 5/2017 | Redler | A61B 17/3421 |
| 2019/0125469 A1* | 5/2019 | Yang | A61B 1/00042 |
| 2019/0209154 A1* | 7/2019 | Richter | A61B 1/00133 |
| 2020/0078068 A1* | 3/2020 | Wall | A61B 17/7082 |
| 2023/0135764 A1* | 5/2023 | Richter | A61B 17/3423 606/90 |

* cited by examiner

*Primary Examiner* — Julianna N Harvey
(74) *Attorney, Agent, or Firm* — Sorell, Lenna & Schmidt, LLP

(57) ABSTRACT

A surgical guide is provided comprising a body defining a first cavity that is configured for disposal of a surgical instrument and an opening. A connector is disposable with the opening and is engageable with a surgical robot. At least one insert is disposable in the first cavity. The at least one insert defines a second cavity configured for disposal of an alternate surgical instrument. Systems, methods, spinal constructs, implants and surgical instruments are disclosed.

20 Claims, 13 Drawing Sheets

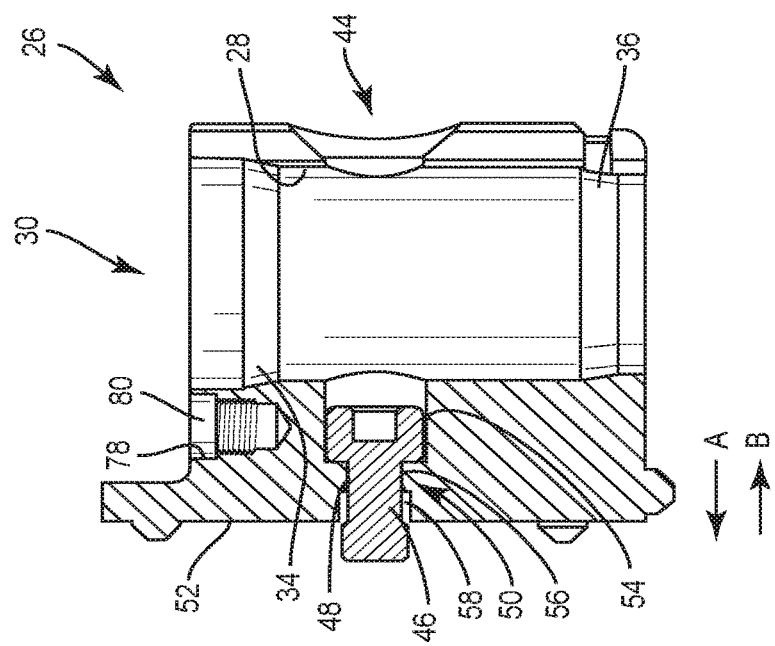
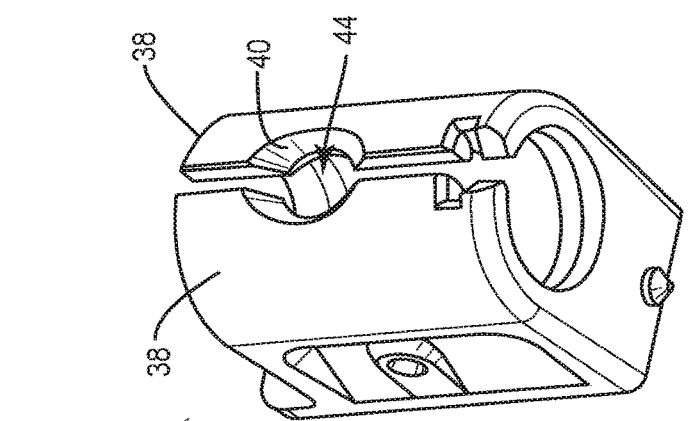
FIG. 3
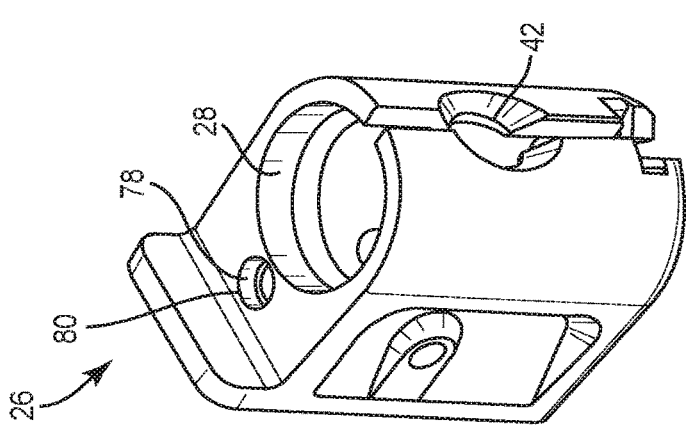
FIG. 2
FIG. 4

SURGICAL GUIDE AND METHODS OF USE

CROSS REFERENCE TO RELATED APPLICATIONS

This application is a divisional of U.S. patent application Ser. No. 16/659,934, filed Oct. 22, 2019, which is expressly incorporated by reference herein, in its entirety.

TECHNICAL FIELD

The present disclosure generally relates to medical devices for the treatment of musculoskeletal disorders, and more particularly to a surgical system and method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, interbody devices can be employed with spinal constructs, which include implants for example bone fasteners and vertebral rods to provide stability to a treated region. These implants can redirect stresses away from a damaged or defective region while healing takes place to restore proper alignment and generally support the vertebral members. During surgical treatment, one or more rods and bone fasteners can be delivered to a surgical site. Surgical instruments are employed, for example, to engage the fasteners for attachment to the exterior of two or more vertebral members. This disclosure describes an improvement over these prior technologies.

SUMMARY

In one embodiment, a surgical guide is provided. The surgical guide comprises a body defining a first cavity configured for disposal of a surgical instrument and an opening. A connector is disposable with the opening and is engageable with a surgical robot. At least one insert is disposable in the first cavity and defines a second cavity configured for disposal of an alternate surgical instrument. In some embodiments, methods, systems, spinal constructs, implants and surgical instruments are disclosed.

In one embodiment, the surgical guide comprises a modular arm guide defining a first cavity configured for disposal of a surgical instrument and an opening. A screw is disposable with the opening and is engageable with a surgical robot. At least one collet is disposable in the first cavity and defines a second cavity configured for disposal of an alternate surgical instrument. The at least one collet is selected from a plurality of alternate collets and the plurality of collets are disposable with the first cavity such that the plurality of collets are interchangeable with the first cavity.

In one embodiment, a surgical system is provided. The surgical system comprises a body defining a first cavity configured for disposal of a surgical instrument and an opening. A connector is disposable with the opening and is engageable with a surgical robot. At least one insert is disposable in the first cavity and defines a second cavity configured for disposal of an alternate surgical instrument. An extender is engageable with the body and the at least one insert.

BRIEF DESCRIPTION OF THE DRAWINGS

The present disclosure will become more readily apparent from the specific description accompanied by the following drawings, in which:

FIG. 2 is a perspective view of components of one embodiment of a surgical system in accordance with the principles of the present disclosure;

FIG. 3 is a perspective view of the components shown in FIG. 2;

FIG. 4 is a side cross section view of the components shown in FIG. 2;

DETAILED DESCRIPTION

Figure 1:
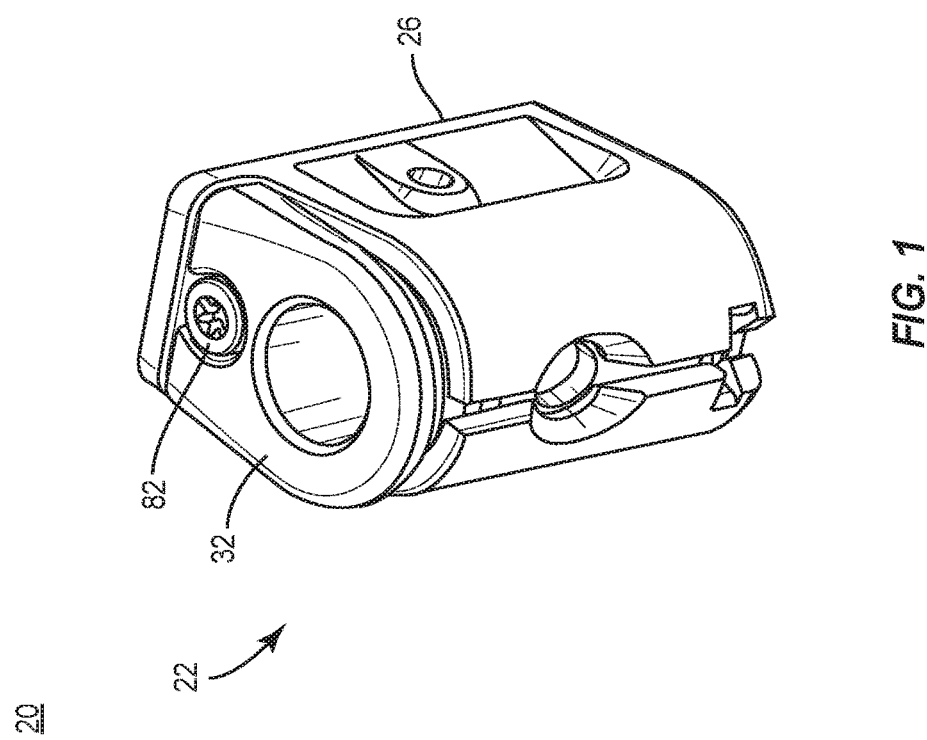
FIG. 1 is a perspective view of components of one embodiment of a surgical system in accordance with the principles of the present disclosure.

The exemplary embodiments of a surgical system are discussed in terms of medical devices for the treatment of musculoskeletal disorders and more particularly, in terms of a surgical system and a method for treating a spine. In some embodiments, the present surgical system comprises an image guided, robot assisted spinal implant system. In some embodiments, the systems and methods of the present disclosure comprise surgical robotic guidance, surgical navigation and medical devices including surgical instruments and implants that are employed with a surgical treatment, as described herein, for example, with a cervical, thoracic, lumbar and/or sacral region of a spine.

In some embodiments, the present surgical system comprises a surgical guide connectable with a surgical robot, surgical robotic guidance, surgical navigation and/or medical devices. In some embodiments, the present surgical system comprises a surgical guide or an arm guide having a cavity that is engageable with a collet selected from a plurality of collets. Each of the plurality of collets includes a cavity, where each of the cavities have different inner diameters compatible with selected surgical instruments. In some embodiments, the plurality of collets are interchangeable within the cavity of the guide to allow a user to implement various surgical instruments during a single surgery. In some embodiments, the present surgical system enables the placement of shank only screws and/or shank and head assemblies in the same surgery.

In some embodiments, a modular arm guide is provided that is configured to receive different sized collets to change an inside diameter of a cavity of the arm guide. In some embodiments, the arm guide remains fixed to a robot in a surgery and the surgery maintains a sterile field.

In some embodiments, the arm guide includes a slot for guidewire procedures. In some embodiments, the arm guide includes a cavity having an inner surface that is at least partially tapered. In some embodiments, the taper can be a 12 degree taper to maintain collet centering and to eliminate tolerance stack up. In some embodiments, the arm guide includes an axial aperture, for example, a threaded hole and a clamp. The threaded hole and the clamp are configured for clamping the collet with the arm guide.

In some embodiments, a plurality of different sized interchangeable collets are provided that are configured for disposal within a cavity of the arm guide, each collet being configured for supporting one or more surgical instruments having a selected diameter. In some embodiments, the surgical system includes a collet that includes a cavity having an inside diameter that is compatible with one or more surgical instruments having a selected size and/or configuration, for example, a selected diameter for disposal within the collet. In some embodiments, the one or more surgical instruments have a 5.5/6.0 mm diameter. In some embodiments, the collet includes an undercut to facilitate removal of the collet from a cavity of the arm guide. In some embodiments, the collet includes a clamp screw that is threaded. In some embodiments, the collet includes a cavity.

In some embodiments, the cavity of the collet has an inner surface that is at least partially tapered. In some embodiments, the inner surface of the cavity of the collet includes a 12 degree tapering. In some embodiments, the one or more surgical instruments have a 4.75 mm diameter. In some embodiments, the surgical system includes a 9 mm collet. In some embodiments, the collet includes a guidewire slot. In some embodiments, the collet includes a flange that is engageable with the clamp. In some embodiments, during manufacture, after the clamp is threaded into the flange, threads of the clamp are fixed with a pin to prevent the clamp from backing out of the flange. In some embodiments, the clamp is a clamp screw.

In some embodiments, the arm guide can be removed or assembled with the collet disposed within the cavity of the arm guide. In some embodiments, the arm guide is retained/removed by a surgical driver that is accessed from a front of the arm guide through an opening. In some embodiments, the arm guide can include a clamp screw to retain a surgical instrument with the arm guide.

In some embodiments, the collet is attached to the arm guide. In some embodiments, when the collet is fully inserted into the cavity of the arm guide, the clamp screw is raised and partially extends out of the flange. In some embodiments, tightening the clamp screw locks the collet in place. In some embodiments, the collet can be removed from the arm guide. In some embodiments, the clamp screw is rotated in a direction to remove it from the flange. In some embodiments, the undercut of the collet can be gripped by a user's fingers to remove the collet from the cavity of the arm guide.

In some embodiments, the surgical system includes an extender for a robotic arm. In some embodiments, the extender mates with the arm guide. In some embodiments, an end of the extender accommodates the size of the arm guide engaged with the collet and clamp screw. In some embodiments, the extender can be used with existing target extender screws.

In some embodiments, the present surgical system is employed with a method of performing robotically-assisted spinal surgery. In some embodiments, the method includes the step of delivering posterior spinal instrumentation through robotic-assisted trajectory alignment tools. In some embodiments, the present surgical system and method includes surgical robotic guidance having robotic software that performs registration of a patient anatomy to a three dimensional working space of a robot.

In some embodiments, the system of the present disclosure may be employed to treat spinal disorders, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including surgical robotic guidance, surgical navigation, surgical instruments, spinal constructs, implants, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-25, there are illustrated components of a surgical system 20.

The components of surgical system 20 can be fabricated from biologically acceptable materials suitable for medical applications, including metals, synthetic polymers, ceramics and bone material and/or their composites. For example, the components of surgical system 20, individually or collectively, can be fabricated from materials for example stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, for example GUM METAL®), ceramics and composites thereof for example calcium phosphate (e.g., SKELITE™), thermoplastics for example polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics for example calcium phosphate, tri-calcium phosphate (TCP), hydroxyapatite (HA)-TCP, calcium sulfate, or other resorbable polymers for example polyaetide, polyglycolide, polytyrosine carbonate, polycaroplaetohe and their combinations.

The components of surgical system 20, individually or collectively, may also be fabricated from a heterogeneous material for example a combination of two or more of the above-described materials. The components of surgical system 20 may be monolithically formed, integrally connected or include fastening elements and/or instruments, as described herein.

Surgical system 20 can be employed, for example, with a minimally invasive procedure, including percutaneous techniques, mini-open and open surgical techniques to manipulate tissue, deliver and introduce instrumentation and/or components of spinal constructs at a surgical site within a body of a patient, for example, a section of a spine. In some embodiments, one or more of the components of surgical system 20 are configured for engagement with existing spinal constructs, which may include spinal implants for example one or more rods, fasteners, plates and connectors. In some embodiments, the spinal constructs can be attached with vertebrae in a revision surgery to manipulate tissue and/or correct a spinal disorder, as described herein.

Figure 25:
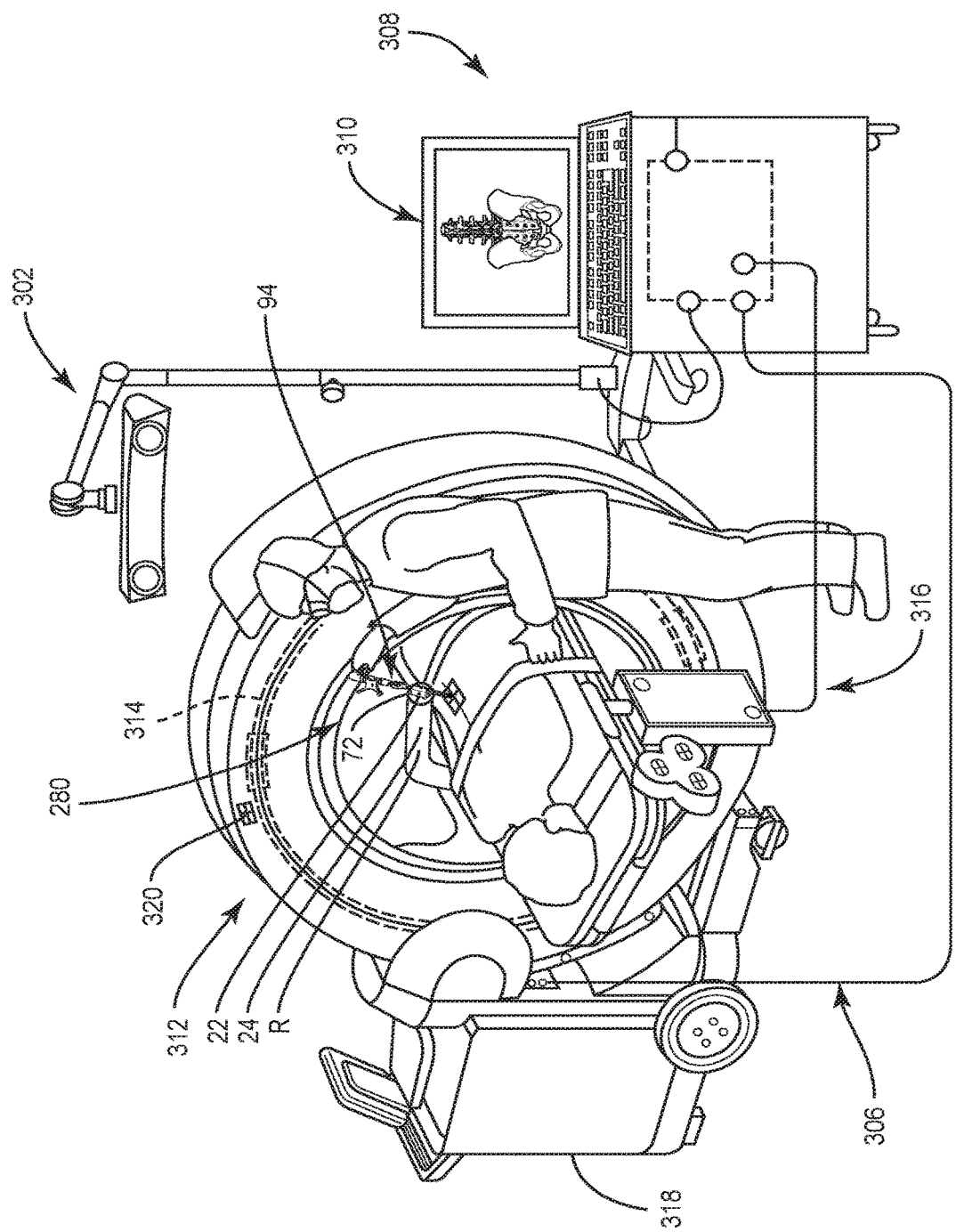
FIG. 25 is a perspective view of components of one embodiment of a surgical system in accordance with the principles of the present disclosure.

Surgical system 20 includes a surgical robotic guidance system having a surgical guide, for example, an end effector 22 connected to a robotic arm 24, as shown in FIG. 25. The surgical robotic guidance system is employed with one or a plurality of surgical instruments for manipulating vertebral tissue, and for delivering and introducing components of spinal constructs for engagement with the vertebral tissue.

End effector 22 includes a body 26, as shown in FIG. 1. Body 26 is a modular arm guide and is configured to fix with a surgical robot R during a surgery, as described herein. Body 26 includes an inner surface 28 that defines a cavity 30. Cavity 30 is configured for engagement with at least one insert, for example, a collet 32, passage of a spinal construct and/or a surgical instrument, as described herein. Cavity 30 has a cylindrical cross-section configuration. In some embodiments, cavity 30 may have various cross section configurations, for example, oval, oblong, triangular, rectangular, square, polygonal, irregular, uniform, non-uniform, variable, tubular and/or tapered.

Surface 28 defines a circumferential taper 34 and a circumferential taper 36 that is spaced apart from circumferential taper 34, as shown in FIG. 4. Circumferential tapers 34, 36 facilitate a central alignment of collet 32 within cavity 30, as described herein. In some embodiments, tapers 34, 36 each include a 12 degree taper. In some embodiments, surface 28 may have various surface configurations, for example, smooth, rough, arcuate, undulating, porous, semi-porous, dimpled, polished and/or textured.

Body 26 includes spaced apart arms 38. Arms 38 extend axially along body 26, as shown in FIG. 3. Arms 38 each include surface 28 and are flexible to facilitate insertion of collet 32, the spinal construct and/or the surgical instrument. In some embodiments, arms 38 have a range or varying degree of flexibility. In some embodiments, arms 38 are not flexible and are rigid. Each arm 38 includes a countersunk surface 40 that defines an opening or recess 42. Recess 42 is disposed lateral to cavity 30 and forms a passageway 44 to provide access to a connector, for example, a clamp screw 46, as described herein. Passageway 44 is configured to guide and/or direct insertion of a surgical instrument, for example, a screw driver (not shown) laterally through cavity 30 to torque, drive or otherwise engage screw 46 to connect end effector 22 with arm 24, as described herein.

Body 26 includes a surface 48 that defines an opening 50. Opening 50 extends from surface 28 to a surface 52 of body 26, as shown in FIG. 4. Opening 50 is disposed in communication with cavity 30 such that screw 46 can be accessed through a portion of cavity 30 for engagement with the driver, as described herein. Opening 50 is configured for translation of screw 46, in the directions shown by arrows A and B in FIG. 4. Opening 50 includes a portion 54, a portion 56 and a portion 58. Portion 54 is disposed in communication with cavity 30 such that screw 46 can be accessed through cavity 30, as shown in FIG. 4. Portion 54 is configured for disposal of a head 60 of screw 46, as described herein.

Figure 15:
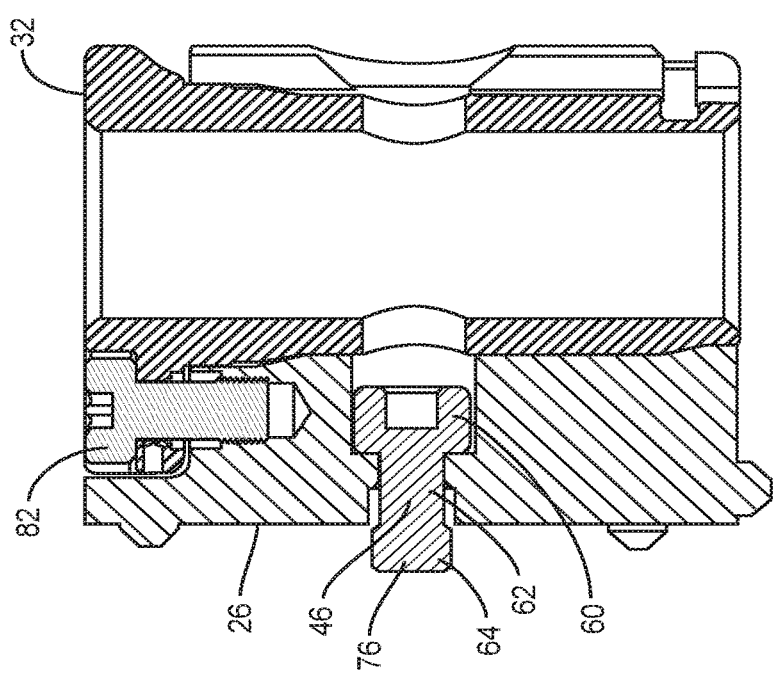
FIG. 15 is a side cross section view of components of one embodiment of a surgical system in accordance with the principles of the present disclosure.

Portion 56 is disposed between portion 54 and portion 58. Portion 56 is configured for disposal of a shaft 62 of screw 46. Portion 58 is disposed in communication with surface 52 of body 26, as shown in FIG. 4. Portion 58 is configured for disposal of a mating portion 64 of shaft 62, as shown in FIG. 15. Portion 58 includes a wall 66 that is configured to limit translation of screw 46 during disengagement of screw 46 from arm 24, for example, as screw 46 translates, in the direction shown by arrow A in FIG. 4, as described herein. Wall 66 limits, resists and/or prevents translation of screw 46 to maintain engagement of head 60 with body 26.

Portions 54, 56, 58 are disposed in axial alignment. Portions 54, 56, 58 include diameters configured to accommodate various sizes of portions of screw 46. Opening 50 is disposed lateral to cavity 30. In some embodiments, opening 50 is disposed at alternate orientations relative to cavity 30, for example, at transverse, perpendicular and/or other angular orientations for example acute or obtuse, and/or may be offset or staggered.

Figure 18:
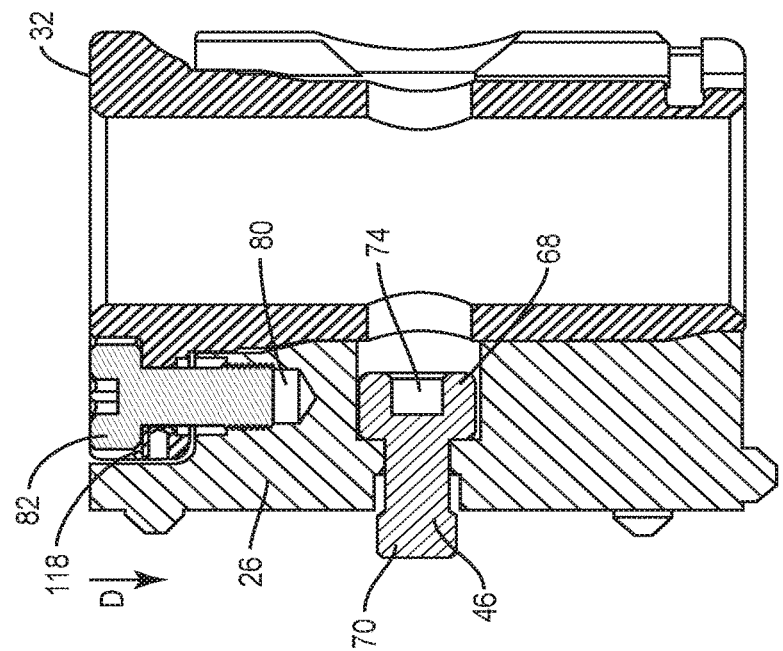
FIG. 18 is a side cross section view of the components shown in FIG. 15.
Figure 17:
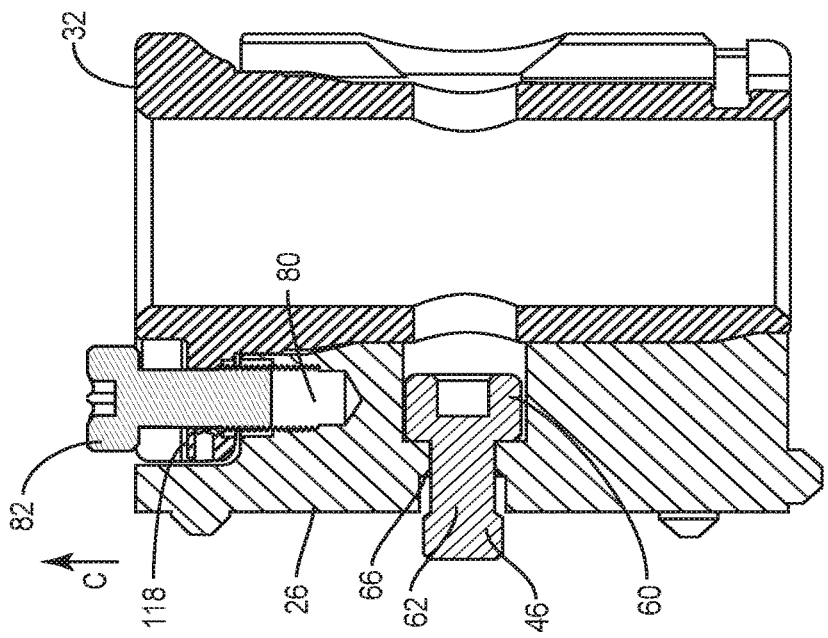
FIG. 17 is a side cross section view of the components shown in FIG. 15.
Figure 19:
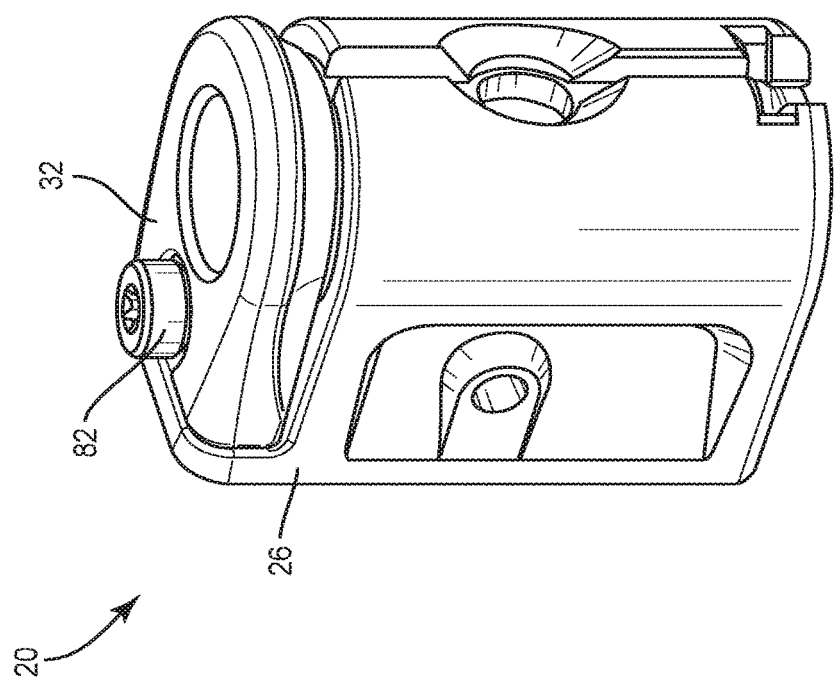
FIG. 19 is a perspective view of components of one embodiment of a surgical system in accordance with the principles of the present disclosure.
Figure 20:
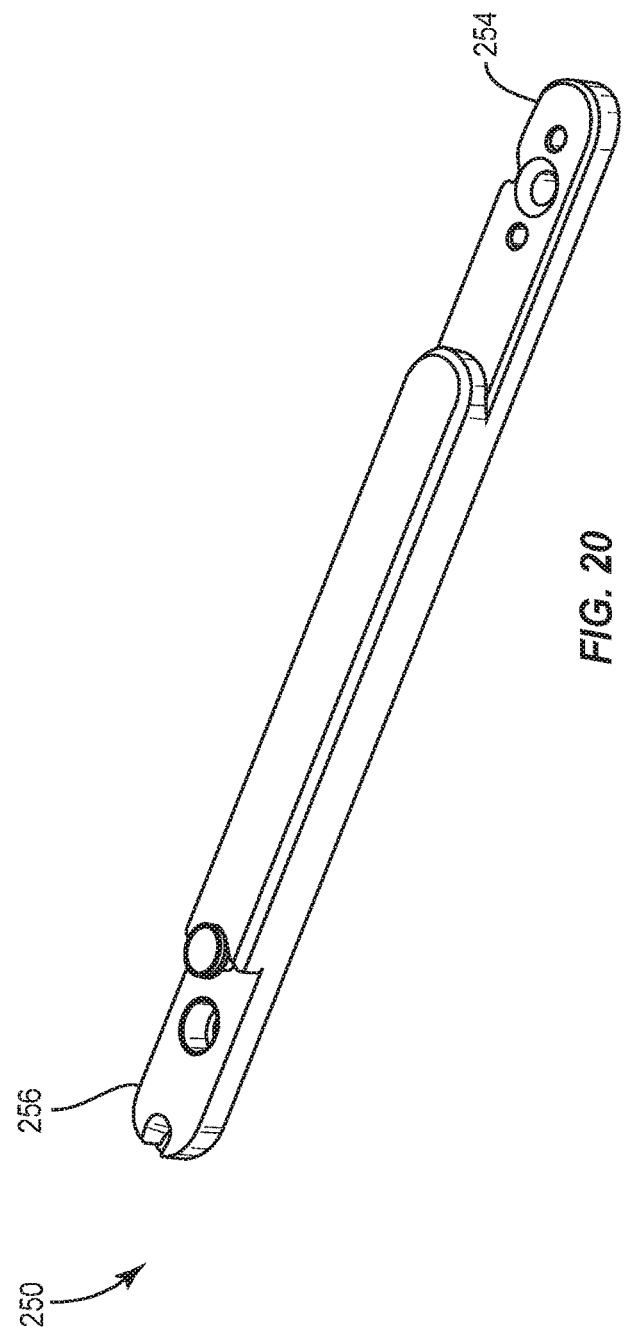
FIG. 20 is a perspective view of components of one embodiment of a surgical system in accordance with the principles of the present disclosure.

Screw 46 extends between an end 68 and an end 70, as shown in FIG. 18. In some embodiments, screw 46 is configured as a clamp screw. Screw 46 is configured to engage a corresponding mating surface 72 of arm 24, to connect end effector 22 with arm 24, as shown in FIG. 25.

Head 60 includes a socket 74, as shown in FIG. 18. Socket 74 is configured for engagement with the driver to drive, torque or otherwise connect screw 46 with arm 24 to assemble end effector 22 with arm 24, as described herein. In some embodiments, socket 74 includes a hexalobe geometry for a mating engagement with a corresponding portion of the driver. In some embodiments, socket 74 can alternatively include a cruciform, phillips, square, hexagonal, polygonal, star cross sectional configuration for disposal of a correspondingly shaped portion of the driver. Screw 46 includes shaft 62 that extends from head 60.

Screw 46 includes mating portion 64 disposed with shaft 62 at end 70. Mating portion 64 includes a surface 76 that is configured for engagement with a portion of arm 24. In some embodiments, surface 76 includes a threaded surface configured for engagement with a threaded surface of arm 24 to facilitate connection of end effector 22 with arm 24. For example, as surface 76 engages a corresponding mating surface 72 of arm 24, screw 46 draws and/or pulls end effector 22 into connection with arm 24.

Body 26 includes a surface 78 that defines an axial aperture 80, as shown in FIG. 2. Aperture 80 is configured for disposal of a clamp 82 to fix collet 32 with body 26, as described herein. Aperture 80 is disposed adjacent and posterior to cavity 30. In some embodiments, surface 78 may be threaded or have various surface configurations, for example, smooth, rough, arcuate, undulating, porous, semi-porous, dimpled, polished and/or textured. In some embodiments, aperture 80 is disposed at alternate orientations relative to cavity 30, for example, at transverse, perpendicular and/or other angular orientations for example acute or obtuse, and/or may be offset or staggered.

Figures 5, 6, 7:
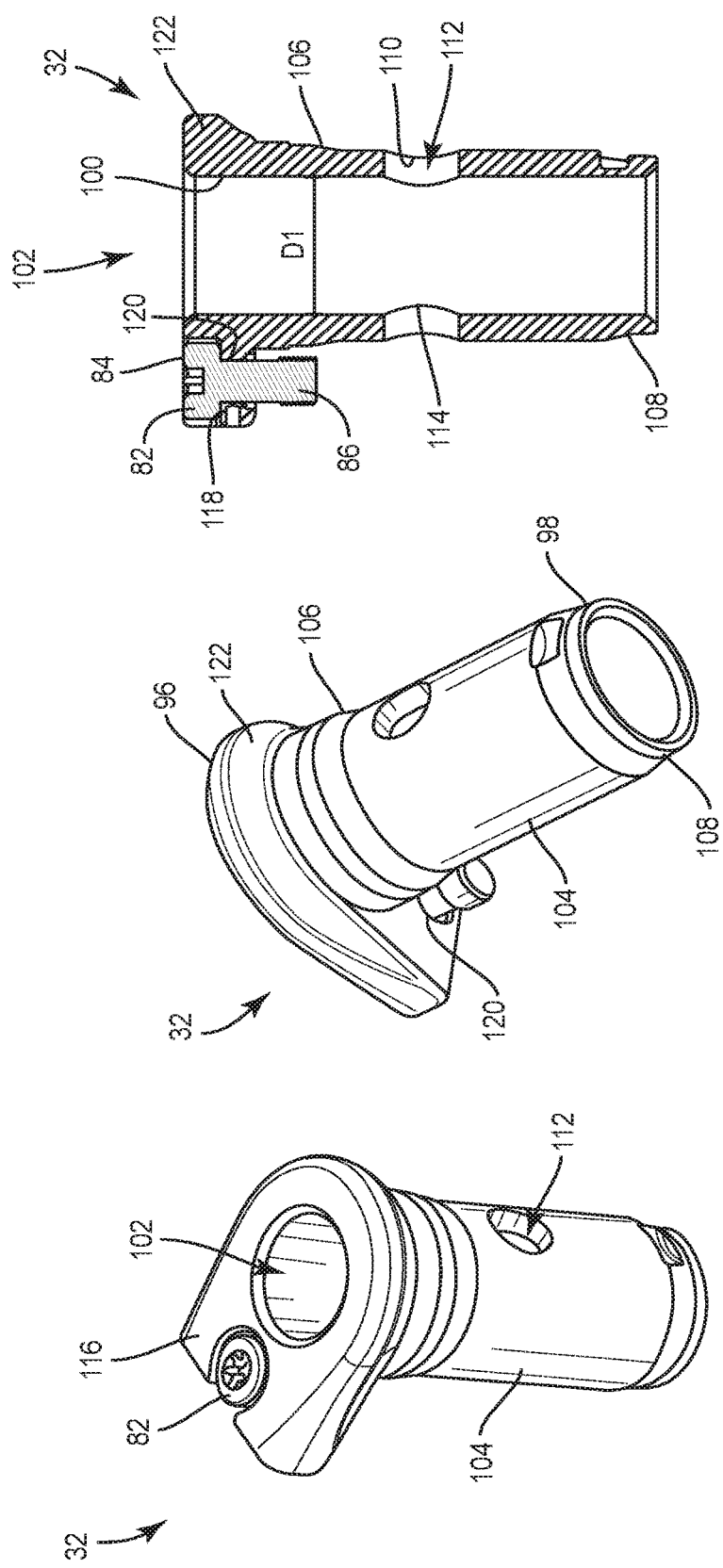
FIG. 5 is a perspective view of components of one embodiment of a surgical system in accordance with the principles of the present disclosure.
FIG. 6 is a perspective view of the components shown in FIG. 5.
FIG. 7 is a side cross section view of the components shown in FIG. 5.
Figure 10:
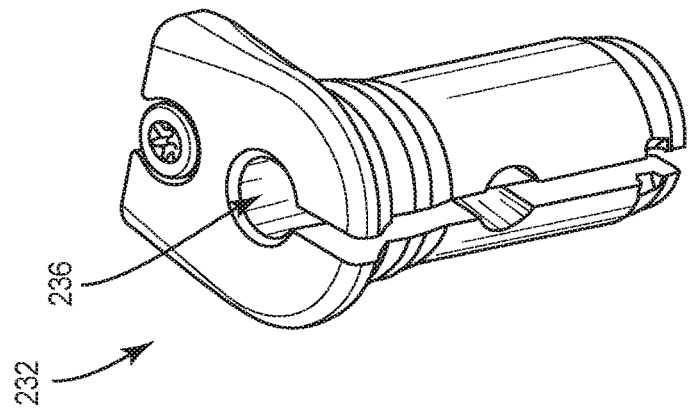
FIG. 10 is a perspective view of components of one embodiment of a surgical system in accordance with the principles of the present disclosure.

Clamp 82 extends between an end 84 and an end 86, as shown in FIG. 7. In some embodiments, clamp 82 is configured as a threaded screw. Clamp 82 includes a head 88 that includes a socket 90. In some embodiments, socket 90 includes a hexalobe geometry for a mating engagement with a corresponding portion of the driver. In some embodiments, socket 90 can alternatively include a cruciform, phillips, square, hexagonal, polygonal, star cross sectional configuration for disposal of a correspondingly shaped portion of the driver. Clamp 82 includes a threaded shaft 92 configured for disposal within aperture 80. In some embodiments, clamp 82 can alternatively be a cam lever and/or fixation of collet 32 with body 26 can be done through a dove tail attachment.

Figure 24:
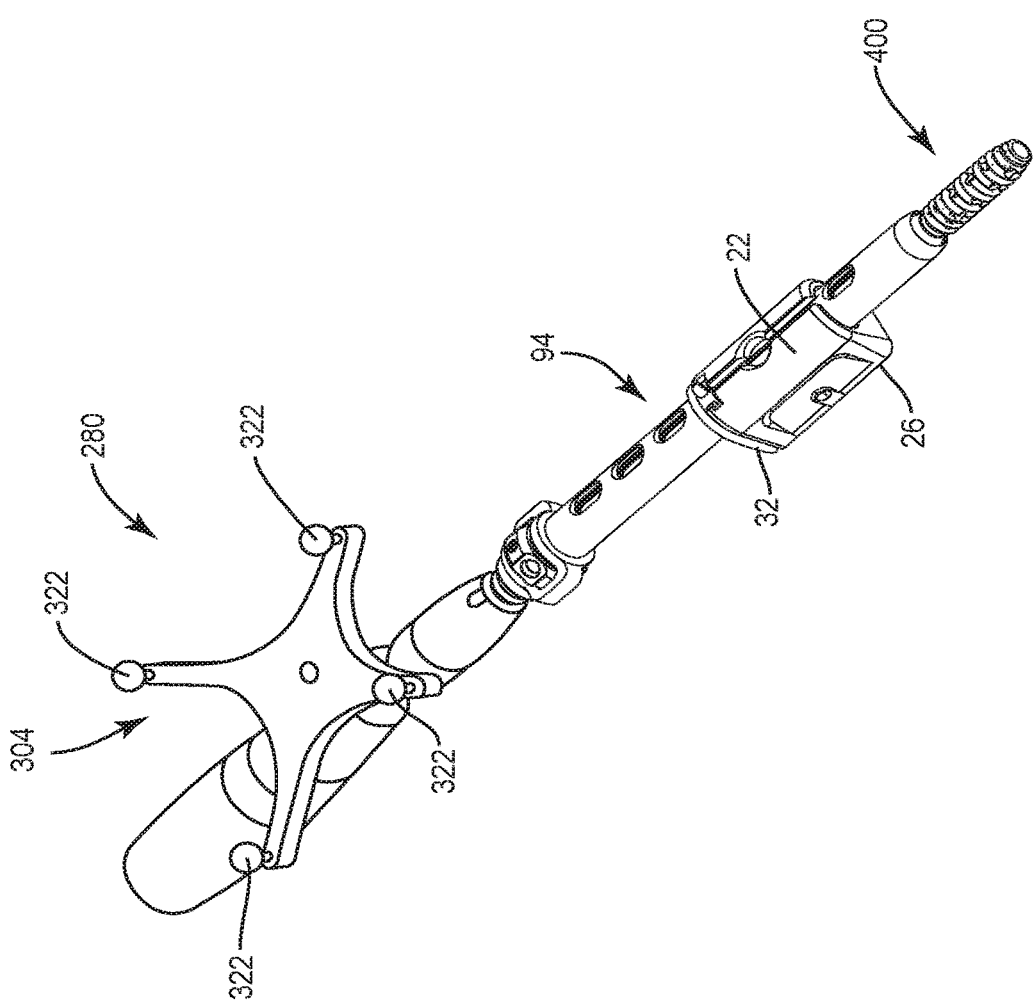
FIG. 24 is a perspective view of components of one embodiment of a surgical system in accordance with the principles of the present disclosure.

End effector 22 includes collet 32, as shown in FIGS. 5-7. Collet 32 is configured for disposal within cavity 30 of body 26 and/or for engagement with a surgical instrument 94, as shown in FIG. 24 and described herein. End effector 22 can be selected from a plurality of alternate collets, for example, collet 132 and collet 232 that are interchangeable with cavity 30, as described herein. Collet 32 extends from an end 96 to an end 98, as shown in FIG. 6. Collet 32 includes an inner surface 100 that defines a cavity 102. Cavity 102 is configured for disposal of a surgical instrument, for example, surgical instrument 94. Cavity 102 is coaxial with cavity 30 and has a cylindrical cross-section configuration. Cavity 102 includes a diameter D1 that is greater than or equal to a diameter of surgical instrument 94. In some embodiments, cavity 102 may have various cross section configurations, for example, oval, oblong, triangular, rectangular, square, polygonal, irregular, uniform, non-uniform, variable, tubular and/or tapered. In some embodiments, surface 100 may have various surface configurations, for example, smooth, rough, arcuate, undulating, porous, semi-porous, dimpled, polished and/or textured.

An outer surface 104 defines a circumferential taper 106 and a circumferential taper 108 that is spaced apart from circumferential taper 106, as shown in FIG. 7. Circumferential tapers 106 and 108 engage circumferential tapers 34, 36 of cavity 30 to facilitate a central alignment of collet 32 within cavity 30. In some embodiments, tapers 106, 108 each include a 12 degree taper.

Surface 104 defines a recess 110. Recess 110 is disposed lateral to cavity 102 and forms a passageway 112 to provide access to clamp screw 46 when collet 32 is disposed in cavity 30, as described herein. Passageway 112 is configured to guide and/or direct insertion of a surgical instrument, for example, the screw driver laterally through cavity 102 to torque, drive or otherwise engage screw 46 to connect end effector 22 with arm 24, as described herein.

Surface 100 defines an opening 114. Opening 114 extends from surface 100 to surface 104, as shown in FIG. 7. Opening 114 is disposed in communication with cavity 102 such that screw 46 can be accessed through a portion of cavity 102 for engagement with the driver, as described herein.

Collet 32 includes a surface 116 that defines a flange 118. Flange 118 is engageable with clamp 82 to fix collet 32 with aperture 80 of body 26, as shown in FIGS. 1 and 15. Head 88 of clamp 82 is configured to be seated within or on flange 118, as shown in FIGS. 1, 5 and 7. Surface 116 defines an opening 120 that is disposed centrally within flange 118 and is configured for disposal of shaft 92 of clamp 82, as shown in FIGS. 6 and 7. Flange 118 is disposed adjacent and posterior to cavity 102. In some embodiments, flange 118 is disposed at alternate orientations relative to cavity 102, for example, at transverse, perpendicular and/or other angular orientations for example acute or obtuse, and/or may be offset or staggered.

Surface 100 defines an undercut 122, as shown in FIG. 6. Undercut 122 is configured for engagement with a user, for example, one or more fingers of a user to facilitate removal of collet 32 from cavity 30. In some embodiments, undercut 122 may have various surface configurations, for example, smooth, rough, dimpled and/or textured.

In use, collet 32 is inserted into cavity 30 of body 26. Head 88 of clamp 82 extends out of flange 118, in a direction shown by arrow C in FIG. 17. Clamp 82 is tightened and head 88 is reduced within flange 118 and shaft 92 of clamp 82 fixes with aperture 80 of body 26, in a direction shown by arrow D in FIG. 18. A driver (not shown) is engaged with passageway 44 and is manipulated to rotate screw 46 into engagement with arm 24. Screw 46 pulls and/or draws end effector 22 for connection with arm 24, as shown in FIG. 25. Surgical instrument 94 can then be disposed within cavity 102 of collet 32.

Figure 9:
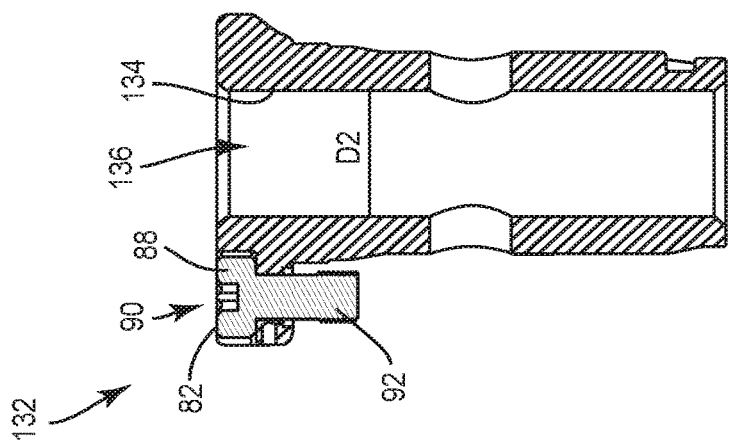
FIG. 9 is a side cross section view of the components shown in FIG. 8.
Figure 8:
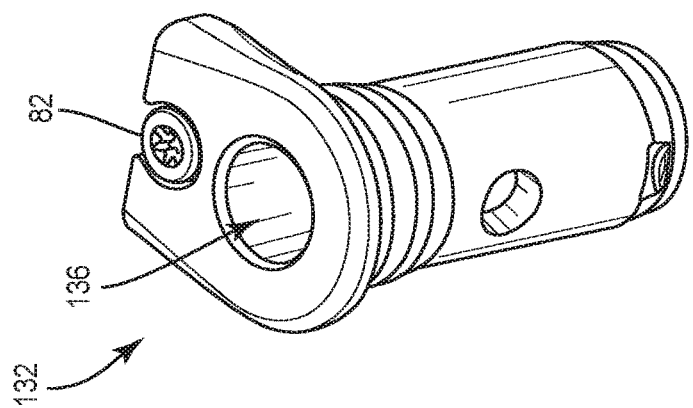
FIG. 8 is a perspective view of components of one embodiment of a surgical system in accordance with the principles of the present disclosure.

As discussed herein, end effector 22 can include a plurality of alternate collets, for example, collet 32, collet 132 and collet 232 that are interchangeable with cavity 30. In some embodiments, alternate collets can be selected for disposal within cavity 30, where each collet includes a different cavity diameter such that various surgical instruments can be employed in the same surgical procedure. For example, in one embodiment, as shown in FIGS. 8 and 9, end effector 22 includes collet 132, similar to collet 32, as described herein. Collet 132 includes an inner surface 134 that defines a cavity 136, similar to surface 100 and cavity 102 of collet 32. Cavity 136 includes a diameter D2 that is greater than or equal to a diameter of a surgical instrument. In some embodiments, diameter D1 of collet 32 is greater than diameter D2 of collet 132.

In one embodiment, as shown in FIGS. 10-14, end effector 22 includes collet 232, similar to collet 32 and collet 132, as described herein. Collet 232 includes an inner surface 234 that defines a cavity 236, similar to surface 100 and cavity 102 of collet 32 and surface 134 and cavity 136 of collet 132. Cavity 236 includes a diameter D3 that is greater than or equal to a diameter of a surgical instrument. In some embodiments, diameter D1 of collet 32 and diameter D2 of collet 132 are greater than diameter D3 of collet 232.

Figure 14:
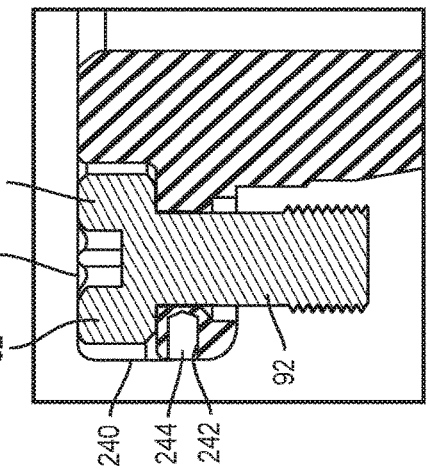
FIG. 14 is an enlarged side cross section view of the components shown in FIG. 13.
Figure 13:
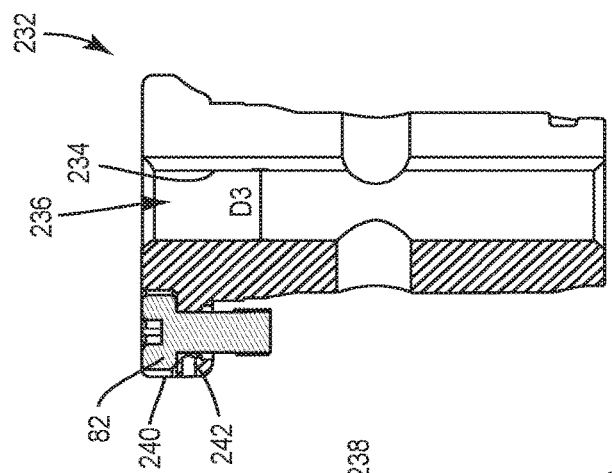
FIG. 13 is a side cross section view of the components shown in FIG. 10.
Figure 12:
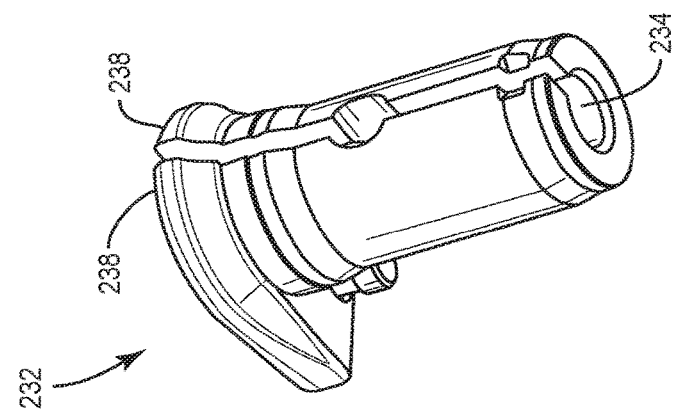
FIG. 12 is a perspective view of the components shown in FIG. 10.
Figure 11:
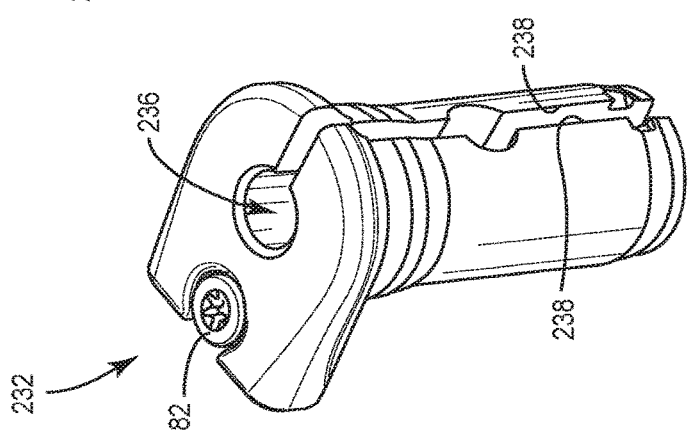
FIG. 11 is a perspective view of the components shown in FIG. 10.
Figure 16:
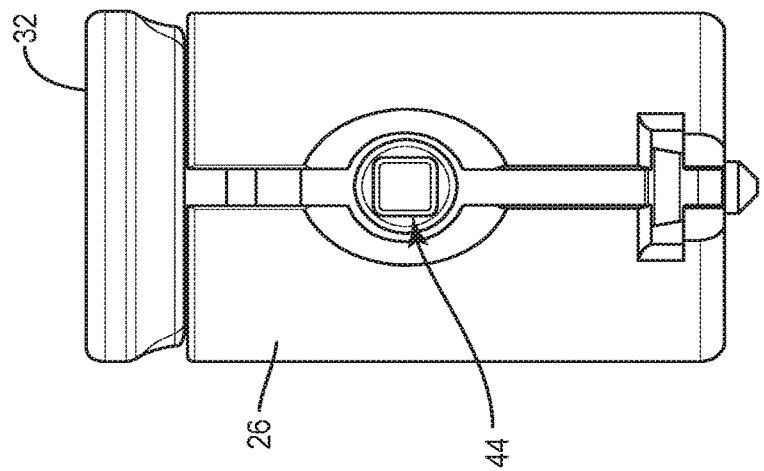
FIG. 16 is a front view of the components shown in FIG. 15.

Collet 232 includes spaced apart arms 238. Arms 238 extend axially along collet 232, as shown in FIG. 12. In some embodiments, arms 238 are flexible and are configured to facilitate insertion of a guidewire (not shown) and/or the surgical instrument. A surface 240 defines an opening 242 configured for disposal of a fixation element, for example, a pin 244, as shown in FIGS. 13 and 14. Pin 244 is configured for engagement with shaft 92 of clamp 82 to fix clamp 82 with flange 118.

In some embodiments, surgical system 20 comprises a surgical kit, which includes a plurality of collets such as collets 32, 132, 232, as described herein. Collets 32, 132, 232 are configured for selection such that collets 32, 132, 232 are engageable and interchangeable with cavity 30 of body 26 to allow a user to implement various surgical instruments during a single surgery.

Figure 21:
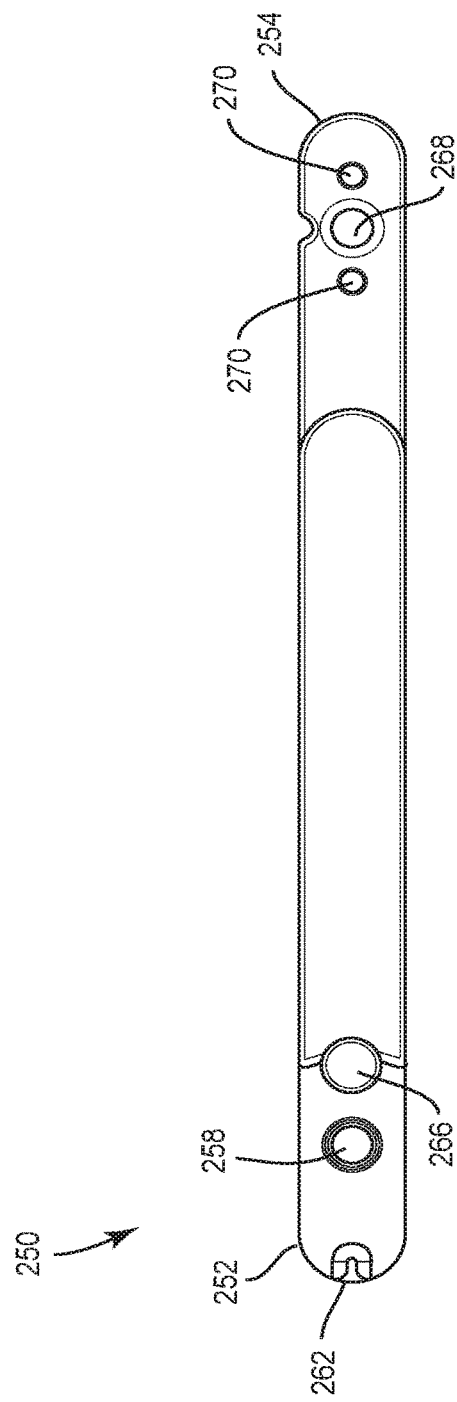
FIG. 21 is a side view of the components shown in FIG. 20.
Figure 22:
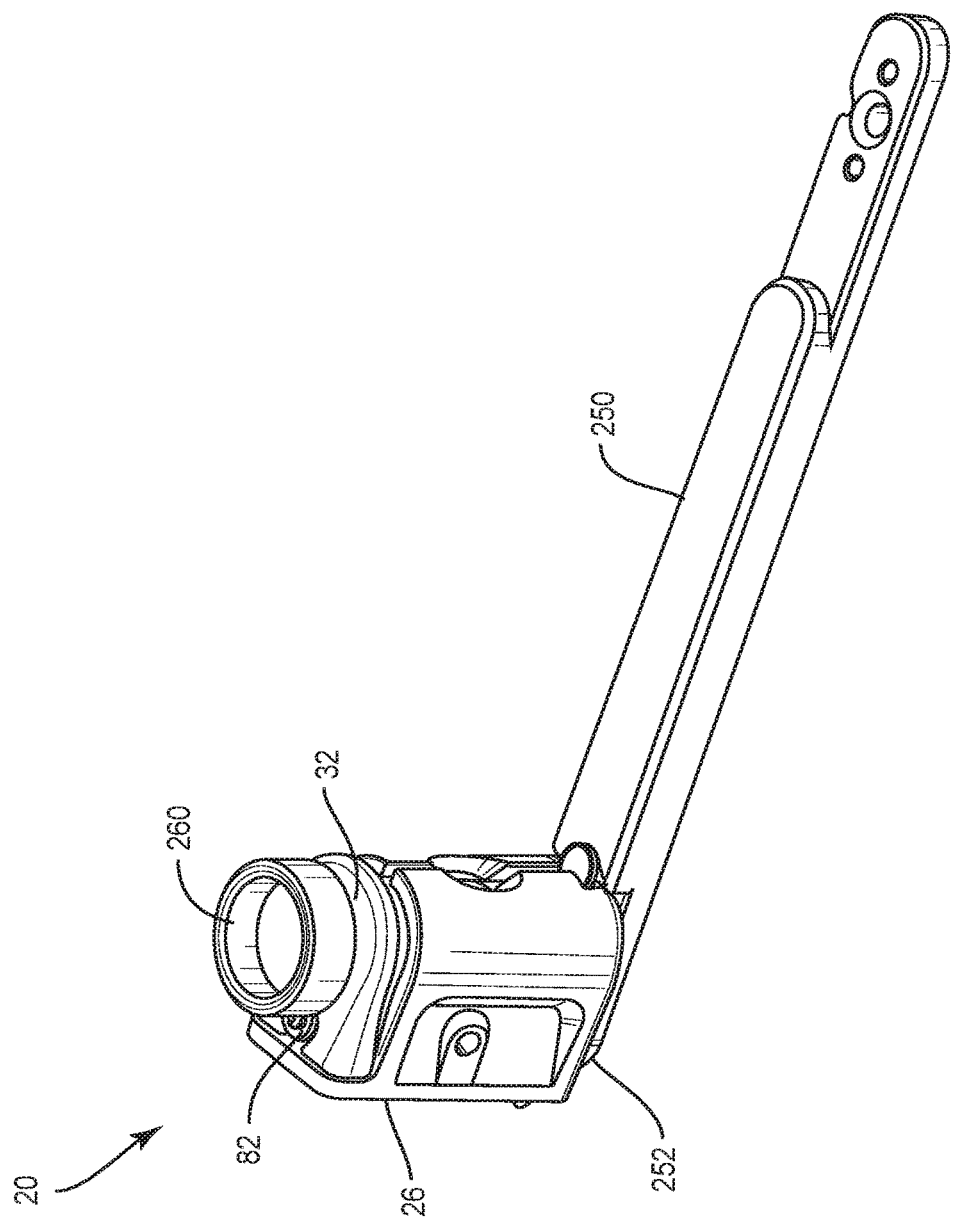
FIG. 22 is a perspective view of components of one embodiment of a surgical system in accordance with the principles of the present disclosure.
Figure 23:
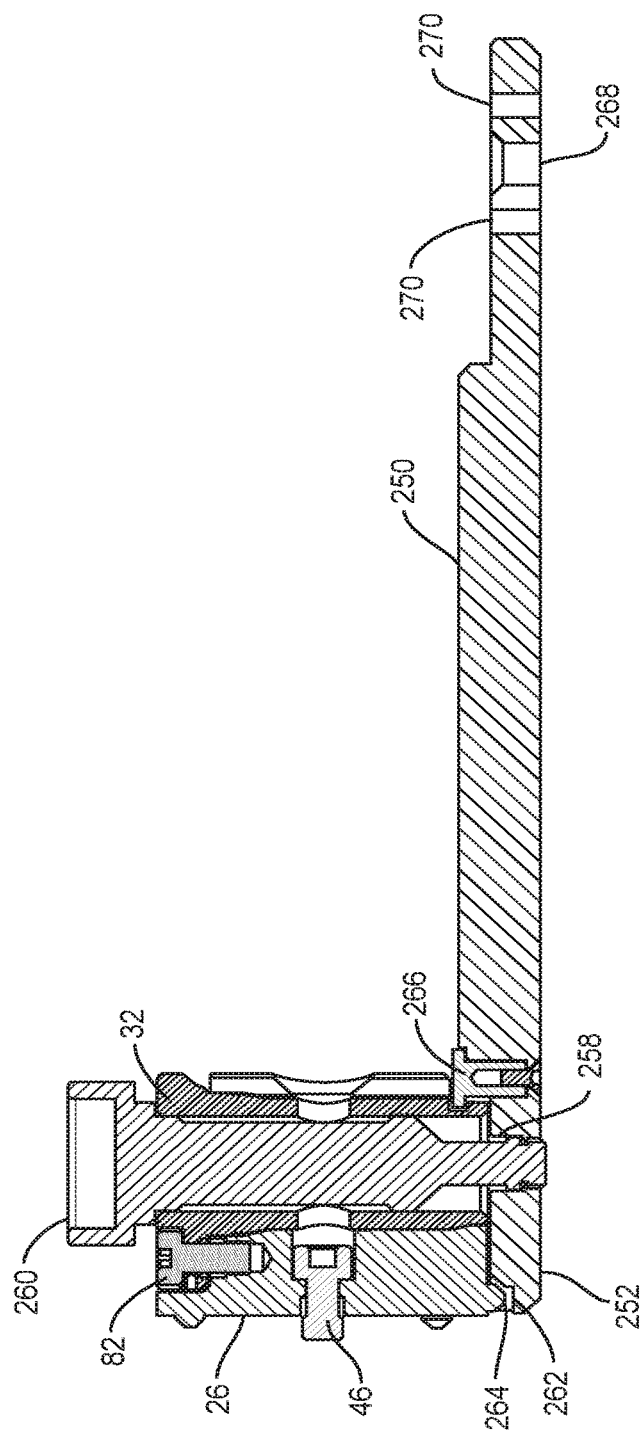
FIG. 23 is a side cross section of the components shown in FIG. 22.

Surgical system 20 includes an extender 250 for arm 24, as shown in FIGS. 20-23. Extender 250 is configured for fixation with arm 24 and engagement with end effector 22. Extender 250 extends between an end 252 and an end 254. End 252 engages with end effector 22. A surface 256 defines a recess 258 at end 252 configured for engagement with an instrument or a target extender screw 260 disposed within cavity 30 of body 26, as shown in FIGS. 21 and 22. Surface 256 defines an indent 262 that is configured for engagement with a projection 264 of body 26, as shown in FIG. 23. A position sensor 266 is disposed on end 252. Surface 256 defines a recess 268 and openings 270 at end 254 configured for fixation with arm 24.

In assembly, operation and use, surgical system 20, similar to the systems and methods described herein, is employed with a surgical procedure, for example, a treatment of an applicable condition or injury of an affected section of a spinal column and adjacent areas within a body. In some embodiments, one or all of the components of surgical system 20 can be delivered or utilized as a pre-assembled device or can be assembled in situ. Surgical system 20 may be completely or partially revised, removed or replaced.

A navigation component 280 is oriented relative to a sensor array 302, as shown in FIGS. 24 and 25, to facilitate communication between navigation component 280 and sensor array 302 during a surgical procedure, as described herein. Navigation component 280 is configured to generate a signal representative of a position of a bone fastener 400 relative to surgical instrument 94, and/or tissue. In some embodiments, the image guide may include human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals.

Navigation component 280 includes an emitter array 304. Emitter array 304 is configured for generating a signal to sensor array 302 of a surgical navigation system 306. In some embodiments, the signal generated by emitter array 304 represents a position of bone fastener 400 relative to surgical instrument 94 and relative to tissue, for example, bone. In some embodiments, the signal generated by emitter array 304 represents a three-dimensional position of bone fastener 400 relative to tissue.

In some embodiments, sensor array 302 receives signals from emitter array 304 to provide a three-dimensional spatial position and/or a trajectory of bone fastener 400 relative to surgical instrument 94 and/or tissue. Emitter array 304 communicates with a processor of a computer 308 of surgical navigation system 306 to generate data for display of an image on a monitor 310, as described herein. In some embodiments, sensor array 302 receives signals from emitter array 304 to provide a visual representation of a position of bone fastener 400 relative to surgical instrument 94 and/or tissue. See, for example, similar surgical navigation components and their use as described in U.S. Pat. Nos. 6,021,343, 6,725,080, and 6,796,988, the entire contents of each of these references being incorporated by reference herein.

Surgical navigation system 306 is configured for acquiring and displaying medical imaging, for example, x-ray images appropriate for a given surgical procedure. In some embodiments, pre-acquired images of a patient are collected. In some embodiments, surgical navigation system 306 can include an O-Arm® imaging device 312 sold by Medtronic Navigation, Inc. having a place of business in Louisville, Colo., USA. Imaging device 312 may have a generally annular gantry housing that encloses an image capturing portion 314.

In some embodiments, image capturing portion 314 may include an x-ray source or emission portion and an x-ray receiving or image receiving portion located generally or as practically possible 180 degrees from each other and mounted on a rotor (not shown) relative to a track of image capturing portion 314. Image capturing portion 314 can be operable to rotate 360 degrees during image acquisition. Image capturing portion 314 may rotate around a central point or axis, allowing image data of the patient to be acquired from multiple directions or in multiple planes. Surgical navigation system 306 can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, surgical navigation system 306 can include C-arm fluoroscopic imaging systems, which can generate three-dimensional views of a patient. The position of image capturing portion 314 can be precisely known relative to any other portion of an imaging device of surgical navigation system 306. In some embodiments, a precise knowledge of the position of image capturing portion 314 can be used in conjunction with a tracking system 316 to determine the position of image capturing portion 314 and the image data relative to the patient.

Tracking system 316 can include various portions that are associated or included with surgical navigation system 306. In some embodiments, tracking system 316 can also include a plurality of types of tracking systems, for example, an optical tracking system that includes an optical localizer, for example, sensor array 302 and/or an EM tracking system that can include an EM localizer. Various tracking devices can be tracked with tracking system 316 and the information can be used by surgical navigation system 306 to allow for a display of a position of an item, for example, a patient tracking device, an imaging device tracking device 320, and an instrument tracking device, for example, emitter array 304, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, and 5,592,939, the entire contents of each of these references being incorporated by reference herein.

Fluoroscopic images taken are transmitted to a computer 318 where they may be forwarded to computer 308. Image transfer may be performed over a standard video connection or a digital link including wired and wireless. Computer 308 provides the ability to display, via monitor 310, as well as save, digitally manipulate, or print a hard copy of the received images. In some embodiments, images may also be displayed to the surgeon through a heads-up display.

In some embodiments, surgical navigation system 306 provides for real-time tracking of the position of bone fastener 400 relative to surgical instrument 94 and/or tissue can be tracked. Sensor array 302 is located in such a manner to provide a clear line of sight with emitter array 304, as described herein. In some embodiments, fiducial markers 322 of emitter array 304 communicate with sensor array 302 via infrared technology. Sensor array 302 is coupled to computer 308, which may be programmed with software modules that analyze signals transmitted by sensor array 302 to determine the position of each object in a detector space.

End effector 22 is fixed to arm 24 of robot R and is configured for disposal with an instrument, for example, surgical instrument 94. Arm 24 includes position sensors (not shown), similar to those referenced herein, which measure, sample, capture and/or identify positional data points of end effector 22 in three-dimensional space for a guide-wireless insertion of for example, bone fastener 400 with tissue. In some embodiments, the position sensors of arm 24 are employed in connection with surgical navigation system 306 to measure, sample, capture and/or identify positional data points of end effector 22 in connection with surgical treatment, as described herein. The position sensors are mounted with arm 24 and calibrated to measure positional data points of end effector 22 in three-dimensional space, which are communicated to computer 308.

Navigation component 280 is oriented relative to sensor array 302, as shown in FIG. 24, to facilitate communication between navigation component 280 and sensor array 302 during the surgical procedure. This configuration provides indicia or display from surgical navigation system 306, as described herein, of components of surgical system 20, and including bone fastener 400 and surgical instrument 94, and their relative positions with tissue in connection with the surgical treatment.

A user selects a single collet that is compatible with surgical instrument 94, for example, collet 32 from the plurality of alternate collets 32, 132 or 232 and inserts collet 32 into cavity 30 of body 26. Surgical instrument 94 is inserted through cavity 102 of collet 32 connected with end effector 22 for insertion to the surgical site. Bone fastener 400 is implanted at the surgical site and surgical instrument 94 is disengaged from bone fastener 400. Surgical instrument 94 is then removed from the surgical site and from cavity 102 of collet 32.

In some embodiments, similarly configured surgical instruments and/or alternately configured surgical instruments, as described herein, may be required for use in the same surgery. In some embodiments, the user can retain collet 32 within cavity 30 of body 26 and insert similarly configured surgical instruments within cavity 102 of collet 32 for use in the same and/or in a different surgical procedure. In some embodiments, alternately configured surgical instruments can be used in the same and/or in a different surgical procedure such that a selected collet, as described herein, is disposed with end effector 22 for receiving the alternately configured surgical instruments. For example, collet 32 is removed from cavity 30 of body 26 and collet 132 is inserted into cavity 30 of body 26 such that compatible surgical instruments can be employed with end effector 22 during the same and/or in a different surgical procedure. In another example, collet 32 or collet 132 is removed from cavity 30 of body 26 and collet 232 is inserted into cavity 30 of body 26 such that compatible surgical instruments can be employed with end effector 22 during the same and/or in a different surgical procedure.

In some embodiments, surgical system 20 includes an agent, which may be disposed, packed, coated or layered within, on or about the components and/or surfaces of surgical system 20. In some embodiments, the agent may include bone growth promoting material, for example, bone graft to enhance fixation of the components and/or surfaces of surgical system 20 with vertebrae. In some embodiments, the agent may include one or a plurality of therapeutic agents and/or pharmacological agents for release, including sustained release, to treat, for example, pain, inflammation and degeneration.

Upon completion of the procedure, the surgical instruments, assemblies and non-implanted components of surgical system 20 are removed from the surgical site and the incision is closed. One or more of the components of surgical system 20 can be made of radiolucent materials for example polymers. Radiomarkers may be included for identification under x-ray, fluoroscopy, CT or other imaging techniques. In some embodiments, one or more surgical instruments can be guided to a surgical site via a guidewire, for example, a K-wire (not shown) and/or without the use of an image guide, as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical guide comprising:
   a modular arm guide defining a first cavity configured for disposal of a surgical instrument, a first opening and a second opening;
   a first screw disposable with the first opening and being engageable with a surgical robot;
   at least one collet disposable in the first cavity and defining a second cavity configured for disposal of an alternate surgical instrument; and
   a second screw disposable with the second opening to fix the at least one collet relative to the modular arm guide,
   wherein the at least one collet is selected from a plurality of alternate collets and the plurality of collets are disposable with the first cavity such that the plurality of collets are interchangeable with the first cavity.

2. A surgical guide as recited in claim 1, wherein the at least one collet includes a flange engageable with a clamp of the modular arm guide to fix the at least one collet with the modular arm guide, the modular arm guide including an axial aperture configured for disposal of the clamp, the clamp including a threaded screw.

3. A surgical guide as recited in claim 1, wherein the modular arm guide includes an inner surface having a first circumferential taper and a second circumferential taper spaced from the first taper.

4. A surgical guide as recited in claim 1, wherein the second cavity of each of the plurality of collets has a different inner diameter.

5. A surgical guide as recited in claim 1, wherein the at least one collet includes spaced apart arms.

6. A surgical guide as recited in claim 5, wherein the spaced apart arms extend axially along the at least one collet.

7. A surgical guide as recited in claim 5, wherein the spaced apart arms are flexible and are configured to facilitate insertion of a guidewire.

8. A surgical guide as recited in claim 1, wherein the plurality of alternate collets are interchangeable with the first cavity for compatibility with selected surgical instruments.

9. A surgical guide as recited in claim 1, wherein the modular arm guide defines a longitudinal axis, the first cavity being axially disposed relative to the longitudinal axis.

10. A surgical guide as recited in claim 1, wherein the modular arm guide is fixed with the surgical robot in a surgery.

11. A surgical system comprising:
    a body defining a first cavity configured for disposal of a surgical instrument, a first opening and a second opening;
    a connector disposable with the first opening and being engageable with a surgical robot; and
    at least one insert disposable in the first cavity and defining a second cavity configured for disposal of an alternate surgical instrument;
    a screw disposable with the second opening to fix the at least one insert relative to the body; and
    an extender engageable with the body and the at least one insert.

12. A surgical system as recited in claim 11, wherein the at least one insert includes a collet, the collet including spaced apart arms.

13. A surgical system as recited in claim 11, wherein the body includes a modular arm guide.

14. A surgical system as recited in claim 13, wherein the modular arm guide includes an inner surface defining a taper.

15. A surgical system as recited in claim 13, wherein the modular arm guide includes an inner surface having a first circumferential taper and a second circumferential taper spaced from the first taper.

16. A surgical guide comprising:
    a body including an inner surface defining a first axial cavity configured for disposal of a surgical instrument, a vertical opening that is spaced apart from the first axial cavity and a transverse opening that is in communication with the first axial cavity;
    a connector disposable with the transverse opening and being engageable with a surgical robot;
    a first screw disposable with the vertical opening;
    at least one collet disposable in the first axial cavity and defining a second cavity configured for disposal of an alternate surgical instrument, the first screw fixing the at least one collet relative to the body; and
    wherein the inner surface of the at least one collet defines a second cavity for disposal of an alternatively configured surgical instrument.

17. A surgical guide as recited in claim 16, wherein the at least one collet comprises spaced apart arms.

18. A surgical guide as recited in claim 16, wherein the body includes a modular arm guide having an inner surface that defines the first axial cavity.

19. A surgical guide as recited in claim 16, wherein the body includes an inner surface defining a taper.

20. A surgical system, comprising:
the surgical guide recited in claim 16; and
the alternatively configured surgical instrument.

* * * * *